United States Patent [19]

Kihara et al.

[11] Patent Number: 4,557,930

[45] Date of Patent: Dec. 10, 1985

[54] ANTICHOLESTEREMIC ANION EXCHANGE RESINS

[75] Inventors: Kunio Kihara; Hideo Toda; Motokuni Mori; Koji Morooka, all of Amimachi, Japan

[73] Assignees: Mitsubishi Petrochemical Co., Ltd.; Mitsubishi Yuka Pharmaceutical Co., Ltd., both of Tokyo, Japan

[21] Appl. No.: 537,387

[22] PCT Filed: Jan. 18, 1982

[86] PCT No.: PCT/JP82/00016

§ 371 Date: Sep. 13, 1983

§ 102(e) Date: Sep. 13, 1983

[87] PCT Pub. No.: WO83/02392

PCT Pub. Date: Jul. 21, 1983

[51] Int. Cl.$^4$ .............................................. A61K 31/74
[52] U.S. Cl. ....................................................... 424/79
[58] Field of Search .......................................... 424/79

[56] References Cited

U.S. PATENT DOCUMENTS

| | | | |
|---|---|---|---|
| 3,769,399 | 10/1973 | Hagerman | 424/79 |
| 3,903,269 | 9/1975 | Kashkina et al. | 424/180 |
| 4,107,098 | 8/1978 | Tamura et al. | 528/407 |
| 4,412,011 | 10/1983 | Kihara et al. | 424/79 |

OTHER PUBLICATIONS

Chemical Abstracts, vol. 96, (1982), #205418w, Mitsubishi.
Journal of Pharmaceutical Sciences, vol. 69, No. 12, (1978), pp. 1695–1698, De Simone et al.

*Primary Examiner*—Leonard Schenkman
*Assistant Examiner*—Joseph A. Lipovsky
*Attorney, Agent, or Firm*—Frishauf, Holtz, Goodman & Woodward

[57] ABSTRACT

This invention relates to an anticholesteremic containing a main ingredient of an anion exchange resin which is a copolymer of an imidazole compound modified with a halomethyl oxirane compound and a polyfunctional epoxy resin, and has an imidazolium salt as the functional group in the main chain.

13 Claims, No Drawings

ANTICHOLESTEREMIC ANION EXCHANGE RESINS

TECHNICAL FIELD

This invention relates to an anticholesteremic, more particularly to an anticholesteremic, comprising a principal ingredient of an epoxy type anion exchange resin having as a functional group an imidazolium salt in the main chain thereof.

BACKGROUND ART

It has been already known in the art to apply an anion exchange resin as the so called anticholesteremic which promotes a reduction of cholesterol levels in the blood (U.S. Pat. Nos. 3,499,960 and 3,780,171; U.K. Pat. No. 929,391; and Japanese Unexamined Patent Publication No. 10386/1978). The mechanism in which cholesterol levels in the blood are reduced may be considered as follows. That is, a basic anion exchange resin immobilizes through adsorption bile acids existing in the intestinal tract to prevent bile acids from being absorbed again, whereby conversion of cholesterol in equilibrium relations with bile acids to bile acids is promoted to result in reduction of cholesterol levels in the blood.

In the prior art, a typical example of a basic anion exchange resin used as anticholesteremic is an ion-exchange resin having an aliphatic quaternary ammonium salt as the functional group (U.S. Pat. Nos. 3,499,960 and 3,780,171). This ion-exchange resin having an aliphatic quaternary ammonium salt as the functional group can be produced by allowing an aliphatic tertiary amine to react with a haloalkyl introduced onto a cross-linked polymer, but the resultant anion exchange resin is accompanied with an objectionable odor inherent in an aliphatic amine and therefore cannot be put into practical uses as such. Thus, in practical applications, a coating is applied on the surface of the anion exchange resin to alleviate the bad odor, but the dosage is obliged to be increased due to the reduction in ion-exchange capacity as the result of the surface coating. Also, such an anion exchange resin of the prior art is low in selective adsorption of bile acids and has the drawback that useful substances such as vitamins are also removed by adsorption.

The present inventors have already invented, as a resin having improved the drawbacks as mentioned above, a polystyrene type anion exchange resin having imidazolium group as the functional group which has a high selective adsorption capacity for bile acids (Japanese Unexamined Patent Publication No. 150017/1981).

On the other hand, along the thought that an anticholesteremic composed principally of an anion exchange resin can be more effective through adsorption of not only bile acids existing in the intestinal tract but also of cholesterol, investigations have been made intensively about a resin having high selective adsorption capacity for bile acids and having further enhanced cholesterol adsorption capacity. As a consequence, this invention has been accomplished.

That is, an object of this invention is to provide a basic anion exchange resin which is free from a bad odor and has selective adsorption capacity for bile acids and cholesterol, and it concerns an anticholesteremic principally composed of an epoxy type anion exchange resin having animidazolium salt in the main chain as the functional group.

SUMMARY OF THE INVENTION

The basic anion exchange resin to be used as the principal ingredient in the anticholesteremic of this invention is a water-insoluble anion exchange resin which is a copolymer of:

(A) a reaction product between a halomethyl oxirane compound represented by the formula [I]:

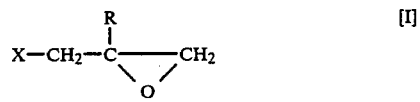

wherein R is a hydrogen atom or a methyl group and X is a halogen atom, and an imidazole of the formula [II]:

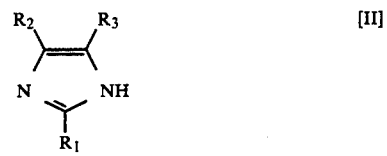

wherein $R_1$ is a hydrogen atom, an alkyl group having 1 to 11 carbon atoms or an aryl group having 6 to 8 carbon atoms; $R_2$ and $R_3$, which may be identical or different, are each a hydrogen atom or an alkyl group having 1 to 3 carbon atoms, and (B) a polyfunctional epoxy resin having two or more oxirane rings and an epoxy equivalence of 100 to 600, having an imidazolium salt as the functional group with the counter-ion being one selected from halogen ion, hydroxyl ion or ½ (sulfate ion).

DETAILED DESCRIPTION OF THE INVENTION

In the above anion exchange resin, the halomethyl oxirane compound is represented by the formula [I]:

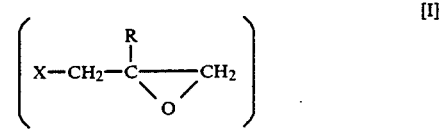

wherein R is a hydrogen atom or a methyl group and X is a halogen atom such as chlorine or bromine.

The imidazoles are represented by the formula [II]:

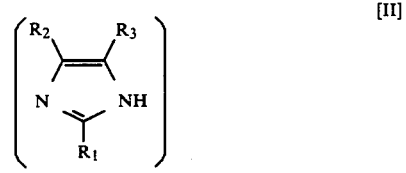

wherein $R_1$ is a hydrogen atom, an alkyl group having 1 to 11 carbon atoms such as methyl, ethyl, propyl, hexyl, undecyl, etc. or an aryl group having 6 to 8 carbon atoms such as phenyl, tolyl, xylyl, etc.; $R_2$ and $R_3$, which may be identical or different, are each a hydrogen atom or an alkyl group having 1 to 3 carbon atoms such as methyl, ethyl, propyl, etc.

The polyfunctional epoxy compound (B) has two or more oxirane rings, referring to those having an epoxy equivalence of 100 to 600, more specifically bisphenol type epoxy resins, novolak type epoxy resins, polyglycol type epoxy resins, carboxylic acid type epoxy resins, amine type epoxy resins or alicyclic type epoxy resins, etc.

The counter-ion in the anion exchange resin of this invention is one selected from halogen ion such as chlorine, bromine, iodine, etc.; hydroxyl ion or ½ (sulfate ion).

The anion exchange resin employed contains a residue of a reaction product between a halomethyl oxirane compound and an imidazole at a content of 30 to 80% by weight, preferably 40 to 70% by weight.

The polymeric substance constituting the anion exchange resin specified by these substituents may have a molecular weight which is not particular limited, so long as it is insoluble in water. Preferable examples of the anion exchange resin of this invention are shown below.

| | Reactive monomers | | | |
|---|---|---|---|---|
| | Halomethyl | Imidazole | | Polyfunctio- | Counter- |
| Sample | oxirane | $R_1$ | $R_2$ or $R_3$ | nal epoxy | ion |
| 1 | | H | H | | $Cl^-$ |
| 2 | | H | H | | $OH^-$ |
| 3 | | H | H | | $Cl^-$ |
| 4 | Epichloro- | $CH_3$ | H | Epikote 828 | $Cl^-$ |
| 5 | hydrin | $C_2H_5$ | $CH_3$ | | $Cl^-$ |
| 6 | | $C_6H_5$ | H | | $Cl^-$ |
| 7 | | $C_{11}H_{23}$ | H | | $Cl^-$ |
| 8 | | H | H | Epikote 154 | $SO_4^{2-}$ |

Also, the anion exchange resin of this invention should preferably have a water content of 30 to 90%, with the particles sizes passable through 50 mesh (Tyler), generally from 50 to 325 mesh.

The anion exchange resin having an imidazolium salt as the functional group can be prepared according to the method as disclosed in Japanese Unexamined Patent Publication No. 151681/1977 (Method for Preparation of Anion Exchange Resin). That is, an anion exchange resin having an imidazolium salt as the functional group can be prepared by allowing a compound having a halomethyl group and an oxirane ring within the molecule to react with an imidazole to prepare a modified imidazole compound, which is in turn made into a resin with a polyfunctional epoxy compound.

(1) Halomethyl oxirane compound:

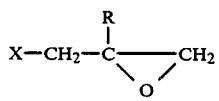

[I]

In the above formula, X is a halogen atom, particularly, chlorine, bromine or iodine atom, and R is a hydrogen atom or a methyl group. Typical examples are epichlorohydrin and β-methyl epichlorohydrin. These can be used in combination.

(2) Imidazoles:

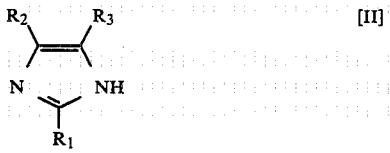

[II]

In the above formula, $R_1$ is a hydrogen atom, an alkyl group having 1 to 11 carbon atoms, a cycloalkyl group or an aryl group; $R_2$ and $R_3$ may be each a hydrogen atom or a $C_1$-$C_3$ alkyl group. The alkyl group or alkyl moiety with no designation of carbon number has generally a carbon number of $C_1$-$C_6$. And, the aryl group is generally phenyl, tolyl or xylyl.

Typical examples of such imidazoles include the following, which may also be used in combination. That is, there are imidazole, 2-methyl imidazole, 2-ethyl imidazole, 2-isopropyl imidazole, 2-undecyl imidazole, 2-phenyl imidazole, 2,4-dimethyl imidazole, 2-ethyl-4-methyl imidazole, 2-phenyl-4-methyl imidazoie and the like.

(3) Preparation of modified imidazoles:

Generally speaking, when a compound having a chloromethyl group and an oxirane ring in the molecule such as epichlorohydrin is allowed to react with an imidazole, an addition product is formed.

A halomethyl oxirane compound is allowed to react in a suitable amount of 0.5 mole or more with one mole of an imidazole.

In order to permit this reaction to proceed smoothly, an organic hydroxy compound may be added in an amount of 10 to 200% by weight based on the imidazole, preferably within the range from 30 to 150% by weight. A hydroxy compound can also act as the catalyst for the reaction to form the modified imidazole in addition to the function as the solvent for imidazoles. The hydroxy compound used in this step was also recognized to have an excellent action as a diluent during the resin formation with a polyfunctional epoxy compound in the subsequent step.

As the hydroxy compound exhibiting such effects, there may be included saturated mono-valent alcohols, particularly primary alcohols having about 1 to 6 carbon atoms such as methanol, ethanol, propanols, butanols; polyvalent alcohols having about 2 to 5 carbon atoms such as ethylene glycol, propylene glycols, butylene glycols, glycerine, diethylene glycol, ethylene glycol monomethyl ether; phenols such as phenol, cresols, xylenols, catachol, resorcin. These may be used in combination.

The structure of the reaction product has not yet been clarified, but it may be considered to be constituted primarily of the following compounds:

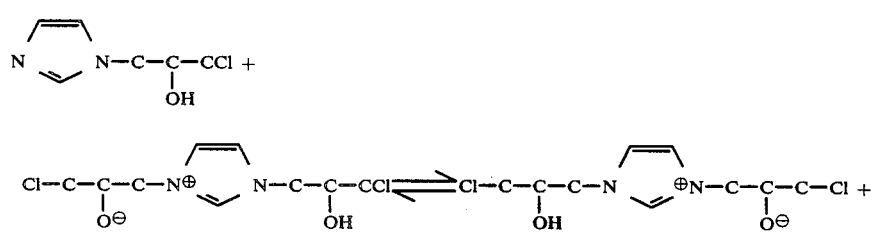

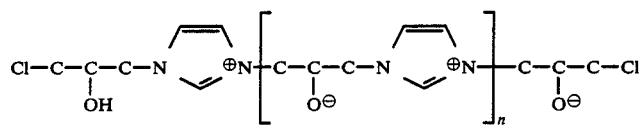

(4) Polyfunctional epoxy compound:

"Polyfunctional" means that the compound has two or more oxirane rings.

A group of polyfunctional epoxy compounds to be suitably used in combination in this invention are those known as so called epoxy resins having an epoxy equivalence of about 100 to 600. Typical examples include the following, namely bisphenol type epoxy resins (e.g. bisphenol A diglycidylether), novolak type epoxy resins (e.g. phenol novolac glycidylether), polyphenol type epoxy resins (e.g. tetrahydroxyphenylethane tetraglycidylether), polyglycol type epoxy resins (e.g. glycerine triglycidylether), carboxylic acid type epoxy resins (e.g. phthalic acid diglycidyl ester), amine type epoxy resins (e.g. glycidylaniline), alicyclic epoxy resins (e.g. vinylcyclohexene diepoxide). These may be used in combination.

(5) Resin formation with polyfunctional epoxy compound:

The heat curing reaction between the modified imidazole as prepared above and a polyfunctional epoxy compound may be carried out by mixing both at predetermined ratios, followed by heating.

In general, polyfunctional epoxy compounds may be used in combination in amounts of 20 to 70% by weight, preferably 30 to 60% by weight based on the total amount with the modified imidazoles, and heating effected at 60° to 190° C., preferably 70° to 180° C. The heating time is about 3 to 15 hours. The heat curing may be carried out in the presence of a diluent, and an example of such a diluent is a hydroxy compound as mentioned above.

(6) Granulation of anion exchange resin formed:

According to the above reaction, there is manufactured a resin mass of an anion exchange resin, which is in turn granulated into an appropriated particle size.

A means for crushing is to crush the resin mass by means of a ball mill or other crushing devices.

Another means for crushing utilizes the characteristic of the ion-exchange resin of this invention, comprising permitting the resin mass to be hydrated in a large amount of an aqueous medium, thereby effecting self-disintegration.

As the aqueous medium, other than water, there are methanol, ethanol and others, and the hydration temperature may be about 20° to 100° C.

After granulation, soluble unaltered reactants are removed by washing successively with a dil. acid (e.g. ca. 0.05–2N inorganic acid such as hydrocholoric acid, sulfuric acid or nitric acid) and a dil. alkali (e.g. ca. 0.05–2N alkali hydroxide such as sodium hydroxide, potasium hydroxide or ammonium hydroxide) (the order of washing may optionally be selected), finally washed thoroughly with pure water, followed by drying, to give granulate anion exchange resin.

When the particle size of the resin granulated by self-disintegration through hydration of the resin mass in a large amount of an aqueous medium is not sufficiently small, the particles can further be subjected to crushing by means of a crushing means such as ball mill or other crushing devices to be granulated into suitable particle sizes.

The polymer formed into a resin may take various structures depending on the epoxy resin employed, but it is estimated to have the following structure, when there is employed an epoxy resin using bisphenol A:

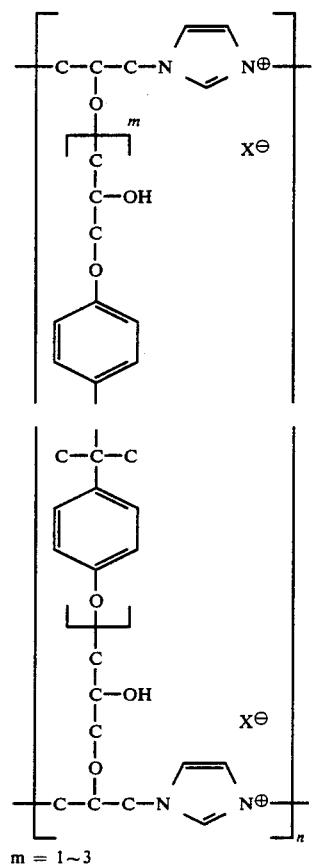

m = 1~3

The thus prepared anion exchange resin has approximately the following characteristics:
Ion-exchange capacity: 2.0–5.0 meq/g.
Water content: 30–90%.
Particle size: 50–325 mesh.

These various properties were measured based on the methods as described in the Preparation example 1 shown below.

The essential feature as anticholesteremic of the epoxy type anion exchange resin having an imidazolium salt as the functional group in the main chain of this invention is in the first place high activity for absorption of bile acids (high even in the co-presense of inorganic ions), as described in detail in the following Test examples. Secondly, it has high cholesterol absorption ability. Thirdly, it has a good serum lipid lowering action, with potent arteriosclerosis suppressing action.

Fourthly, it is odorless. Further characteristic can be seen in smaller adsorption of useful substances (Vitamin $B_1$).

The reason for the above-mentioned good selective adsorption of bile acids, cholesterol adsorption, serum lipid lowering action and arteriosclerosis action has not yet been clarified, but it may be estimated that the resonance structure of the imidazolium salt and the skeletal structure of the epoxy type resin having an imidazolium salt in the main chain will contribute greatly to such effects.

Next, the acute toxicity of the anion exchange resin of this invention is to be explained.

When a suspension of the resin in a dispersant of 1% tragacanth solution was administered orally to ICR-JCL-strain mouse, the $LD_{50}$ value determined from mortality after one week was 5 g/Kg or more.

The anticholesteremic of this invention may be administered at a dose of 0.5 to 30 g, preferably 2 to 20 g, per human adult per day, usually in 2 to 3 divided doses per day.

The anticholesteremic of this invention can be administered to a human body ordinarily by the route of oral administration. In case of oral administration, it may be administered before a meal in the state of a suspension in water or other liquids.

BEST MODES FOR PRACTICING THE INVENTION

This invention is to be described in further detail by referring to the following Preparation examples and Test examples, in order to clarify its effects.

PREPARATION EXAMPLE 1

(i) Into a four-necked flask equipped with a reflux condenser, a thermometer and a stirrer were charged 25 g (0.37 mole) of imidazole, 25 ml of ethanol and 5 ml of ethylene glycol to prepare a homogeneous mixture. While maintaining the reaction temperature at 55° to 60° C. under stirring, 30 g (0.32 mole) of epichlorohydrin was added dropwise over about 30 minutes, followed further by stirring for 5 hours, to obtain a modified imidazole.

(ii) After 50 parts of the above modified imidazole and 50 parts of Epikote 828 (WPE:180, produced by Shell Chemical Co.) which is a bifunctional epoxy compound were homogeneously mixed, the mixture was cured by heating at 80° C. for one hour and at 180° C. for 5 hours. The cured product was left to cool and put into water, whereby it was readily disintegrated by hydration to give granular resins. The granules formed were washed successively under stirring and heating at about 80° C. with 3% caustic soda and with 3% hydrochloric acid to remove soluble unaltered substances, followed finally by thorough washing with pure water. Then, the product was dried by heating and the resin obtained was crushed in a ball mill.

The anion exchange resin obtained (abbreviated as CR - 1) had the following characteristics:
Ion-exchange capacity : 3.8 meq/g.
Water content: 69.4%.
Particle size: 200–325 mesh.

The various characteristics as mentioned above have been determined according to the methods as described below.

Ion-exchange capacity: the value of total exchange capacity shown by the sum of neutral salt decomposing capacity and moderately weak base capacity.

(a) Neutral salt decomposing capacity: About 3 g of a resin is sampled, immersed in 100 ml of 1.0N NaOH solution for 5 hours and washed with water until neutral. After drying under reduced pressure, 2–3 g of a dry resin is precisely weighed (this weight is defined as A g), and 100 ml of 0.5N-NaCl solution is added thereto and the mixture after stirring for 4 hours is left to stand overnight. After suction filtration, the filtrate is titrated with 0.1N-HCl solution (the amount of 0.1N-HCl solution consumed in this titration is defined as B ml). The neutral salt decomposing capacity is determined by the following formula:

Neutral salt decomposing capacity
(meq/g)=B×(factor of HCl solution)/10 A (b) Moderately weak base capacity: The resin remaining on the funnel is placed in 100 ml of 0.2N-HCl solution, and after left to stand overnight, 10 ml of the supernatant is sampled and titrated with 0.1N-NaOH solution (the amount of 0.1N-NaOH solution required in this titration is defined as C ml). Further, 10 ml of the above 0.2 N-HCl solution is sampled and titrated with 0.1N-NaOH solution (the amount of 0.1N-NaOH solution required is defined as D ml). The moderately weak base capacity is determined by the following formula:

Moderately weak base capacity
(meq/g)=(D−C)×(factor of NaOH solution)/A

Water content: An amount of 5–10 g of the resin is immersed in pure water overnight, and thereafter subjected to suction filtration on a funnel until cracks are formed on the resin layer surface, followed by weighing of the hydrous resin (Wa). The weight of the resin after drying at 50° C. under reduced pressure for 8 hours (Wb), and the water content is determined from the following formula:

Water content=(Wa−Wb)/Wa×100 (%)

Particle size: Dried resin is crushed for 1 to 2 hours by means of a ball mill produced by Alfred Frisch Co., and the crushed resin is sieved to a predetermined particle size by an electromagnetic sieve shaker for laboratory use.

The properties of the anion exchange resin obtained in the following Preparation examples were also determined according to the above methods.

PREPARATION EXAMPLE 2

After 60 parts of the modified imidazole obtained in Preparation example 1(i) were mixed homogeneously with 40 parts of Epikote 828, the mixture was cured under heating at 80° C. for one hour and at 180° C. for 5 hours. The cured product was left to cool, and then put into water to be readily disintegrated by hydration into a granular resin product. The granular product was subjected to the post-treatment similarly as described in Preparation example 1(ii).

The anion exchange resin obtained (abbreviated as CR-2) had the following characteristics:
Ion-exchange capacity: 3.9 meq/g.
Water content: 73.0%.
Particle size: 200–325 mesh.

PREPARATION EXAMPLE 3

After 70 parts of the modified imidazole obtained in Preparation example 1(i) were mixed homogeneously with 30 parts of Epikote 828, the mixture was cured under heating at 80° C. for one hour and at 180° C. for 5 hours. The cured product was left to cool, and then put into water to be readily disintegrated by hydration into a granular resin product. The granular product was subjected to the post-treatment similarly as described in Preparation example 1(ii).

The anion exchange resin obtained (abbreviated as CR-3) had the following characteristics:
Ion-exchange capacity: 4.2 meq/g.
Water content: 84.0%.
Particle size: 200–325 mesh.

PREPARATION EXAMPLE 4

(i) Into a four-necked flask equipped with a reflux condenser, a thermometer and a stirrer were charged 29 g (0.35 mole) of 2-methylimidazole, 30 ml of ethanol and 5 ml of glycerine to prepare a homogeneous mixture. While maintaining the reaction temperature at 55° to 60° C. under stirring, 30 g (0.32 mole) of epichlorohydrin was added dropwise over about 30 minutes, followed further by stirring for 5 hours, to obtain a modified imidazole.

(ii) After 60 parts of the above modified imidazole and 40 parts of Epikote 828 were homogeneously mixed, the mixture was cured by heating at 80° C. for one hour and at 180° C. for 5 hours. The cured product was subjected to the same post-treatment as described in Preparation example 1(ii). The anion exchange resin obtained (abbreviated as CR - 4) had the following characteristics:
Ion-exchange capacity: 3.4 meq/g.
Water content: 75.7%.
Particle size: 200–325 mesh.

PREPARATION EXAMPLE 5

(i) Into a four-necked flask equipped with a reflux condenser, a thermometer and a stirrer were charged 39 g (0.35 mole) of 2-ethyl-4-methylimidazole, 2 ml of ethanol and 5 ml of ethylene glycol to prepare a homogeneous mixture. While maintaining the reaction temperature at 55° to 60° C. under stirring, 30 g (0.32 mole) of epichlorohydrin was added dropwise over about 30 minutes, followed further by stirring for 5 hours, to obtain a modified imidazole.

(ii) After 60 parts of the above modified imidazole and 40 parts of Epikote 828 were homogeneously mixed, the mixture was cured by heating at 80° C. for one hour and at 180° C. for 5 hours. The cured product was subjected to the same post-treatment as described in Preparation example 1(ii). The anion exchange resin obtained (abbreviated as CR - 5) had the following characteristics:
Ion-exchange capacity: 3.6 meq/g.
Water content: 82.5%.
Particle size: 200–325 mesh.

PREPARATION EXAMPLE 6

(i) Into a four-necked flask equipped with a reflux condenser, a thermometer and a stirrer were charged 51.4 g (0.35 mole) of 2-phenylimidazole, 30 ml of ethanol and 5 ml of ethylene glycol to prepare a homogeneous mixture. While maintaining the reaction temperature at 55° to 60° C. under stirring, 30 g (0.32 mole) of epichlorohydrin was added dropwise over about 30 minutes, followed further by stirring for 5 hours, to obtain a modified imidazole.

(ii) After 60 parts of the above modified imidazole and 40 parts of Epikote 828 were homogeneously mixed, the mixture was cured by heating at 80° C. for one hour and at 180° C. for 5 hours. The cured product was subjected to the same post-treatment as described in Preparation example 1(ii). The anion exchange resin obtained (abbreviated as CR - 6) had the following characteristics:
Ion-exchange capacity: 3.4 meq/g.
Water content: 63.3%.
Particle size: 200–325 mesh.

PREPARATION EXAMPLE 7

(i) Into a four-necked flask equipped with a reflux condenser, a thermometer and a stirrer were charged 79.2 g (0.35 mole) of 2-undecylimidazole, 25 ml of ethanol and 5 ml of ethylene glycol to prepare a homogeneous mixture. While maintaining the reaction temperature at 55° to 60° C. under stirring, 30 g (0.32 mole) of epichlorohydrin was added dropwise over about 30 minutes, followed further by stirring for 5 hours, to obtain a modified imidazole.

(ii) After 60 parts of the above modified imidazole and 40 parts of Epikote 828 were homogeneously mixed, the mixture was cured by heating at 80° C. for one hour and at 180° C. for 5 hours. The cured product was subjected to the same post-treatment as described in Preparation example 1(ii). The anion exchange resin obtained (abbreviated as CR - 7) had the following characteristics:
Ion-exchange capacity: 3.2 meq/g.
Water content: 41.7%.
Particle size: 200–325 mesh.

PREPARATION EXAMPLE 8

After 50 parts of the modified imidazole obtained in Preparation example 1(i) and 50 parts of Epikote 154 (WPE:178, produced by Shell Chemical Co.) were homogeneously mixed, the mixture was cured by heating at 80° C. for one hour and at 180° C. for 5 hours. The cured product was subjected to the same post-treatment as described in Preparation example 1(ii). The anion exchange resin obtained (abbreviated as CR - 8) had the following characteristics:
Ion-exchange capacity: 3.3 meq/g.
Water content: 60.4%.
Particle size: 200–325 mesh.

TEST EXAMPLE 1 in vitro test (1) In vitro test for adsorption of sodium bile salt by various anion exchange resins:

Into an Erlenmeyer flask was charged 30 ml of a solution of sodium bile salt with a concentration of 0.43 mg/ml prepared by use of a phosphate buffer (0.25M, pH 7.5), and each 30 mg of CR - 1, CR - 2, CR - 3, CR - 4, CR - 5, CR - 6, CR - 7, CR - 8, and Cholestyramine was added thereto. After incubation at 37° C. for 24 hours, each mixture was subjected to centrifugation, and the supernatant was recovered. According to the enzyme reaction method (using Sterognost-3$a$-kit: Reagent for assay of bile acid concentration, produced by Daiichi Pure Chemicals Co.), the residual sodium bile salt was quantitatively determined. The results are shown in Table 1.

TABLE 1

| | Proportion of bound bile salt (%) |
|---|---|
| Cholestyramine | 22 |
| CR - 1 | 48 |
| CR - 2 | 45 |
| CR - 3 | 46 |
| CR - 4 | 44 |
| CR - 5 | 49 |
| CR - 6 | 39 |
| CR - 7 | 51 |
| CR - 8 | 40 |

From the results shown in Table 1, it can clearly been seen that the anion exchange resins CR - 1, CR - 2, CR - 3, CR - 4, CR - 5, CR - 6, CR - 7 and CR - 8 can adsorb a large amount of sodium bile salt in a phosphate buffer.

(2) In vitro test for adsorption of sodium bile salt with various kinds of buffers at various concentrations:

Into an Erlenmeyer flask was charged 30 ml of a solution of sodium bile salt with a concentration of 0.43 mg/ml prepared by use of each phosphate buffer (pH 7.5), and 30 mg of each resin was placed into the solution. The adsorption test was practiced according to the method 1) to quantify the residual sodium bile salt. The results are shown in Table 2.

TABLE 2

| | | Proportion of bound bile salt (%) | | |
|---|---|---|---|---|
| Buffer | Conc.(M) | Cholestyramine | CR - 1 | CR - 5 |
| Phosphate | 0 | 90 | 95 | 93 |
| | 0.05 | 23 | 43 | 46 |
| | 0.25 | 29 | 49 | 47 |
| Carbonate | 0.25 | 22 | 45 | 44 |

From the results shown in Table 2, the anion exchange resins CR - 1 and CR - 5 of this invention are small in dependence on concentration of adsorption lowering in phosphate buffer and also have higher adsorption capacity in carbonate buffer.

That is, the anion exchange resin of this invention can adsorb selectively bile acids even in the presence of various inorganic ions. This suggests that the anion exchane resin of this invention is very useful in the the intestinal tract where various inorganic ions are present.

(3) In vitro test for adsorption of sodium bile salt at various pH:

Into an Erlenmeyer flask was charged 30 ml of a solution of sodium bile salt with a concentration of 0.43 mg/ml prepared by use of phosphate buffers with various pH values, and 30 mg of each resin was placed into the solution. The adsorption test was practiced according to the method (1) to quantify the residual sodium bile salt. The results are shown in Table 3.

TABLE 3

| Phosphate buffer | | Proportion of bound bile salt (%) | | |
|---|---|---|---|---|
| (M) | pH | Cholestyramine | CR - 1 | CR - 5 |
| 0.0 | 5.0 | 96 | 100 | 100 |
| | 6.0 | 91 | 95 | 94 |
| | 7.0 | 88 | 90 | 92 |
| | 8.0 | 90 | 90 | 90 |
| 0.25 | 6.0 | 32 | 50 | 51 |
| | 7.0 | 24 | 50 | 49 |
| | 8.0 | 29 | 49 | 48 |

From the results in Table 3, it can clearly been seen that the anion exchange resins of this invention have high adsorption capacity for sodium bile salts under the conditions approximate to those in a living body (within the intestinal tract), namely a buffer concentration of 0.25M and pH 6–8.

(4) In vitro test for adsorption of cholesterol by various anion exchange resins:

In a test tube were placed 2 ml of a cholesterol solution with a concentration of 2 mg/ml dissolved in dimethylformamide and 1 ml of a buffer (HCl-Tris-aminomethane, pH 8.0), and further 20 mg of a resin was added. After shaking at room temperature for 30 minutes, the mixture was centrifuged and 2 ml of the supernatant was sampled. To this sample was added 4 ml of a chloroform-methanol (2:1) solution, and after shaking for 20 minutes, the mixture was centrifuged. The supernatant was sampled and the residual cholesterol was quantified according to the UV-absorption method [using Cholesterol Test Wako Kit, produced by Wako Pure Chemical Industries Co.]. The results are shown in Table 4.

TABLE 4

| | Proportion of bound cholesterol (%) |
|---|---|
| Cholestyramine | 2.8 |
| CR - 1 | 76.5 |
| CR - 5 | 70.0 |

From the results in Table 4, it can be understood that the anion exchange resins of this invention have cholesterol adsorption capacity.

(5) In vitro test for adsorption of Vitamin $B_1$ by various anion exchange resins.

Into an Erlenmeyer flask was charged 30 ml of an aqueous Vitamin $B_1$ hydrochloride solution with a concentration of 0.34 mg/ml, and 30 mg each of various anion exchange resins was added thereto. After incubation at 37° C. for 6 hours, the mixture was centrifuged and the supernatant was sampled for quantitative determination of the residual Vitamin $B_1$ according to the UV-method (268 nm). The results are shown in Table 5.

TABLE 5

| | Proportion of bound Vitamin $B_1$ (%) |
|---|---|
| Cholestyramine | 14 |
| CR - 1 | 2 |
| CR - 5 | 3 |

From the results in Table 5, it can be seen that the adsorption of Vitamin $B_1$ by the anion exchange resin of this invention is small.

TEST EXAMPLE 2

In vivo tests by mouse

Five male ICR - JOL mice, weighing about 18 g, were used per each group. To the first group of mice was given 2 g/10 g-body weight/day of a mixture of a powdery feed for mouse produced by Kurea Japan Inc. mixed with 1% of cholesterol and 0.5% of bovine bile powders, and to the mice of the second, third and fourth groups were further given CR - 1, CR - 5 and Cholestyramine, respectively. The resin employed was mixed in the feed at a level of 2.5%. Seven days after administration of high cholesterol feed and the medicament, blood was sampled from the eye ground vein of mouse, and the total cholesterol content in the centrifuged plasma was quantitatively determined by use of the Cholesterol Test Wako Kit produced by Wako Pure Chemical Industries Co. The results are shown in Table 6.

TABLE 6

| | Total plasma cholesterol (mg/dl) | Inhibition (%) |
|---|---|---|
| Control | 105.2 ± 2.1 | 100 |
| 1% Cholesterol intake | 164.8 ± 5.1 | 0 |
| 1% Cholesterol intake + Cholestyramine | 132.5 ± 5.3** | 54.2 |
| 1% Cholesterol intake + CR - 1 | 112.0 ± 4.6** | 88.6 |
| 1% Cholesterol intake + CR - 5 | 115.1 ± 5.2** | 83.4 |

**$p < 0.01$

From these data, it can clearly been seen that the anion exchange resin of this invention has anticholesteremic action in a living body.

TEST EXAMPLE 3

In vivo tests by rabbit

Five to seven male New Zealand species rabbits, weighing about 2.2 Kg, were used per each group. To the first group of rabbits was given 40 g/Kg-body weight/day of a mixture of a feed produced by Oriental Yeast Co. mixed with 0.67% of cholesterol, and to the rabbits of the second and third groups were further given CR - 1 and Cholestyramine, respectively. The resin employed was mixed in the feed at a level of 0.5%.

Seven days and 14 days after administration of high cholesterol feed and the medicament, blood was sampled from the pinnal vein of rabbit, and the total cholesterol content in the centrifuged plasma was quantitatively determined by use of the Cholesterol Test Wako Kit produced by Wako Pure Chemical Industries Co. The results are shown in Table 7.

TABLE 7

| | After 7 days | | After 14 days | |
|---|---|---|---|---|
| | Total plasma cholesterol[1] | Inhibition[2] | Total plasma cholesterol[1] | Inhibition[2] |
| Control | 44.0 ± 5.1 | 100 | 50.6 ± 6.1 | 100 |
| 0.67% Cholesterol intake | 378.0 ± 33.0 | 0 | 684.0 ± 34.0 | 0 |
| 0.67% Cholesterol intake + CR - 1 | 254.6 ± 30.6** | 36.9 | 410.5 ± 38.1** | 43.2 |
| 0.67% Cholesterol intake + Cholestyramine | 381.3 ± 40.7 | 0 | 703.8 ± 56.2 | 0 |

[1] mg/dl,
[2] %,
**$p < 0.01$

From these results, it can be seen that the anion exchange resin of this invention has a potent anticholesteremic action in a living body (rabbit).

TEST EXAMPLE 4

In vivo tests by rabbit (Arteriosclerosis inhibition test)

Eight to fourteen male New Zealand species rabbits, weighing about 2.2 Kg, were used per each group. To the first group of rabbits was given 40 g/Kg-body weight/day of a mixture of a feed produced by Oriental Yeast Co. mixed with 0.67% of cholesterol for 12 weeks, and to the rabbits of the second and third groups were further given CR - 1 and Clofibrate, respectively.

CR - 1 and Clofibrate employed was mixed in the feed at levels of 1.25% and 0.25%, respectively.

During the tests, the plasma lipid concentrations were measured, and after 12 weeks, all the rabbits were sacrificed by bleeding. Descending aorta were subjected to incision and the conditions of arteriosclerosis were observed. The results are shown in Table 8.

TABLE 8

| | Control (8 rabbits) | 0.67% Cholesterol intake (13 rabbits) | 0.67% Cholesterol intake + CR - 1 (9 rabbits) | 0.67% Cholesterol intake + Clofibrate (14 rabbits) |
|---|---|---|---|---|
| Total plasma: | | | | |
| Cholesterol (mg/dl) | | | | |
| 6 weeks | 45.1 ± 5.2*** | 1571 ± 60 | 595 ± 85** | 1810 ± 124 |
| 12 weeks | 37.0 ± 4.8*** | 1941 ± 123 | 1131 ± 158** | 1895 ± 117 |
| β-Lipoprotein (mg/dl) | | | | |
| 6 weeks | 87.1 ± 28.1*** | 4209 ± 249 | 842 ± 104*** | 5038 ± 450 |
| 12 weeks | 84.4 ± 11.9*** | 4636 ± 341 | 2322 ± 359** | 4385 ± 574 |
| Triglyceride (mg/dl) | | | | |
| 6 weeks | 45.0 ± 6.7*** | 247.1 ± 36.2 | 61.1 ± 17.7*** | 337.1 ± 66.1 |
| 12 weeks | 57.5 ± 5.7*** | 339.6 ± 37.5 | 159.8 ± 28.6** | 336.8 ± 39.7 |
| Aorta: | | | | |
| Total area of (cm²) (12 weeks) | 16.7 ± 0.9* | 19.0 ± 0.5 | 17.1 ± 0.4* | 17.7 ± 0.5 |
| Area of blood vessel at arteriosclerolysis (cm²) (12 weeks) | 0 | 10.5 ± 1.1 | 3.7 ± 1.2** | 8.0 ± 1.4 |
| Percentage of arteriosclerolysis (%) (12 weeks) | 0 | 53.9 ± 4.9 | 21.6 ± 6.4** | 44.2 ± 7.0 |
| Inhibition of arteriosclerolysis | — | 0 | 59.9 | 18.0 |

TABLE 8-continued

|  | Control (8 rabbits) | 0.67% Cholesterol intake (13 rabbits) | 0.67% Cholesterol intake + CR - 1 (9 rabbits) | 0.67% Cholesterol intake + Clofibrate (14 rabbits) |
| --- | --- | --- | --- | --- |
| (%) (12 weeks) | | | | |

Percentage of arteriosclerolysis = (Area at arteriosclerolysis)/(Total blood vessel area) × 100;
*t < 0.05,
**t < 0.01,
***t < 0.001

As apparently seen from the Table, the anion exchange resin of this invention exhibits inhibiting action against increase of plasma lipids (total cholesterol, β-lipoprotein, triglyceride).

Further, particularly effective is the fact that the group of rabbits administered with CR - 1 was 21.6% in percentage of arteriosclerosis, indicating about 60% of arteriosclerosis inhibiting action, as contrasted to the group of rabbits to which is given 0.67% cholesterol feed with a percentage of arteriosclerosis of 53.9%. The plasma lipid lowering action by the anion exchange resin of this invention may be considered to be due to the effect of inhibiting absorption of cholesterol.

Also, in view of the marked inhibition of generation of arteriosclerosis, the anion exchange resin of this invention may be estimated to be utilizable as a lipid lowering agent and an arteriosclerosis preventive agent.

We claim:

1. A method of reducing the level of cholesterol in blood, which comprises administering to a human being an anticholesteremic amount of a composition containing a water-insoluble anion exchange resin in combination with a pharmaceutically acceptable carrier, said water-insoluble anion exchange resin being a copolymer of:

(A) a reaction production of a halomethyl oxirane compound represented by formula (I):

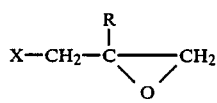

[I]

wherein R is a hydrogen atom or a methyl group and X is a halogen atom, and an imidazole compound of formula (II):

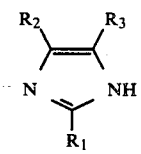

[II]

wherein $R_1$ is a hydrogen atom, an alkyl group having 1 to 11 carbon atoms or an aryl group having 6 to 8 carbon atoms; $R_2$ and $R_3$, which may be identical or different, are each a hydrogen atom or an alkyl group having 1 to 3 carbon atoms, and (B) a polyfunctional epoxy resin having at least two oxirane rings and an epoxy equivalence of 100 to 600, said anion exchange resin having an imidazolium salt as the functional group with the counter-ion being selected from the group consisting of a halogen ion, a hydroxyl ion and ½ (sulfate ion).

2. The method according to claim 1, wherein said polyfunctional epoxy resin is selected from the group consisting of bisphenol type epoxy resins, novolak type epoxy resins, polyglycol type epoxy resins, carboxylic acid type epoxy resins, amine type epoxy resins and alicyclic type epoxy resins.

3. The method according to claim 1, wherein the anion exchange resin has a water content of 30 to 90% and particle sizes of 50 mesh or lower.

4. The method according to claim 1, wherein the halomethyl oxirane compound is selected from the group consisting of epichlorohydrin, methylepichlorohydrin and a mixture of epichlorohydrin and methylepichlorohydrin.

5. The method according to claim 1, wherein the anion exchange resin contains from 30 to 80% by weight of said reaction product.

6. The method according to claim 5, wherein the anion exchange resin contains from 40 to 70% by weight of said reaction product.

7. The method of claim 1, wherein said composition is administered to said human being at a dose of 0.5 to 30 g/day of said water-insoluble anion exchange resin.

8. The method according to claim 7, wherein said composition is administered to said human being at a dose of 2 to 20 g day of said water-soluble anion exchange resin.

9. The method according to claim 1, wherein said composition is administered orally in the form of a suspension.

10. A method of reducing the level of cholesterol in blood, which comprises administering to a human being an anticholesteremic amount of a composition containing a water-insoluble anion exchange resion in combination with a pharmaceutically acceptable carrier, said water-insoluble anion exchange resin being a copolymer of:

(A) a reaction product of a halomethyl oxirane compound being at least one compound selected from the group consisting of epichlorohydrin and methylepichlorohydrin in an amount of 30 to 80% by weight based on the total weight of said water-insoluble anion exchange resin and an imidazole of formula (II):

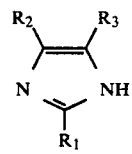

wherein $R_1$ is a hydrogen atom, an alkyl group having 1 to 11 carbon atoms or an aryl group having 6 to 8 carbon atoms; R2 and R3, which may be identical or different, are each a hydrogen atom or an alkyl group having 1 to 3 carbon atoms, and (B) a polyfunctional epoxy resin having at least two oxirane rings and an epoxy equivalence of 100 to 600, and being selected from the group consisting of bisphenol type epoxy resins, novolak type epoxy resins, polyglycol type epoxy resins, carboxylic acid type epoxy resins, amine type epoxy resins and alicyclic type epoxy resins,
said anion exchange resin having an imidazolium salt as the functional group with the counter-ion being selected from a halogen ion, a hydroxyl ion or ½ (sulfate ion) and said anion exchange resin having a water content of 30 to 90% and particle sizes of 50 mesh or lower.

11. The method of claim 10, wherein said composition is administered to said human being at a dose of 0.5 to 30 g/day of said water-soluble anion exchange resin.

12. The method according to claim 11, wherein said composition is administered to said human being at a dose of 2 to 20 g day of said water-soluble anion exchange resin.

13. The method according to claim 10, wherein said composition is administered orally in the form of a suspension.

* * * * *